United States Patent [19]
Eikelmann et al.

[11] 3,931,307
[45] Jan. 6, 1976

[54] PROCESS FOR THE STABILIZATION OF METHIONINE

[75] Inventors: Gerd Eikelmann, Grossauheim; Rudolf Fahnenstich, Mombris; Theodor Lussling, Grossauheim; Sven-Peter Mannsfeld, Steinbach; Gerhard Pohl; Herbert Tanner, both of Grossauheim; Hans Wagner, Constance, all of Germany

[73] Assignee: Deutsche Gold- und Silber-Scheideanstalt vormals Roessler, Germany

[22] Filed: Nov. 30, 1973

[21] Appl. No.: 420,574

[30] Foreign Application Priority Data
Dec. 2, 1972  Germany............................ 2259159

[52] U.S. Cl. ............................................ 260/534 S
[51] Int. Cl.$^2$..................................... C07C 149/247
[58] Field of Search................................. 260/534 S

[56]  References Cited
UNITED STATES PATENTS
2,432,429  12/1947  Lecky.............................. 260/534 S OTHER PUBLICATIONS
Chemical Abstracts, Vol. 55, 4504h, (1961).
Greenstein and Winitz, Chemistry of the Amino Acids, Vol. 3, pp. 2137–2139, (1961).

Primary Examiner—Richard L. Raymond
Attorney, Agent, or Firm—Cushman, Darby & Cushman

[57]  ABSTRACT
Methionine is stabilized by adjusting the pH to the range from 3 to <5. The source of the hydantoin is preferably 5-(beta-methylmercaptoethyl)-hydantoin.

9 Claims, No Drawings

PROCESS FOR THE STABILIZATION OF METHIONINE

The invention is directed to a process for the production of storage stable methionine.

Methionine is generally produced by hydrolysis of the corresponding aminonitrile (alpha amino gamma methylmercapto butyronitrile) or hydantoin (5-beta-methylmercaptoethyl) hydantoin. The hydrolysis is carried out in acid or alkaline medium. The methionine is separated from the solutions resulting from the hydrolysis by neutralization of the solutions to a pH value near the isoelectric point of pH 5.6. According to the type of process and the neutralization agent the pH is from 5 to 6 (Kirkpatrick U.S. Pat. No. 2,443,391) from 5 to 8 (German Pat. No. 891,259 and the corresponding White U.S. Pat. No. 2,557,920) or a pH of 7.2 to 7.8 (German Pat. No. 1,906,405 and corresponding British Pat. No. 1,296,347. The entire disclosures of U.S. Pat. No. 2,443,391, U.S. Pat. No. 2,557,920, German Pat. No. 1,906,405 and British Pat. No. 1,296,347 are hereby incorporated by reference.

The resulting methionine in the separation from the solution is contaminated by inorganic salts and by-products occurring in the hydrolysis. Because of these impurities the methionine is impaired in its storagability, even if there is a relatively small content of impurities. It has an unpleasant odor, discolors after some time, becomes lumpy, can no longer be sprinkled or poured freely and for most purposes is only still of limited utility.

The impurities are only insufficiently removed from the methionine by customary purification processes such as washing and recrystallization. Processes which treat the reaction mixture resulting from the hydrolysis by extraction with alcohol) Kralovec U.S. Pat. No. 2,504,425) with acid cation exchange resins, e.g. a sulfonated styrene-ethyl vinyl benzene-divinyl benzene copolymer, (White U.S. Pat. No. 2,700,054) or which subject the reaction mixture to dialysis (German Auslegeschrift 1,543,845) before the methionine is separated from the reaction mixture in the customary manner effect perhaps the elimination of certain individual impurities. These processes are, moreover, expensive.

It has now been found that there can be obtained a storage stable methionine if the pH of the methionine is adjusted to the range of between 3 and less then 5 in the presence of water. By the use of this process methionine which is contaminated with by-products occurring in the hydrolysis and by the inorganic salts formed in the separation from solution can be rendered unlimitedly storage stable. It is unnecessary to completely purify the methionine from these contaminations.

To carry out the process of the invention the methionine, e.g. containing the contaminants mentioned above, is adjusted to a pH of between 3 and less then 5, especially a pH from 3.0 to 4.9, preferably a pH of 4.3 to 4.8. The necessary amount of acid is added to the methionine to accomplish this. There can be used any acid which supplies the required pH and is inert to methionine. These include especially mineral acids such as hydrochloric acid, sulfuric acid, phosphoric acid, and hydrobromic acid. Instead of acids there can also be added acid salts of the acids as for example alkali hydrogen sulfates, e.g. sodium hydrogen sulfate and potassium hydrogen sulfate, etc. The preferred acidic material used is sulfuric acid, phosphoric acid, sodium hydrogen sulfate and sodium dihydrogen phosphate.

According to the process of the invention, there can be stabilized methionine which is present as a dry material, for example as a commercial product, as a wet material or as a paste or as a solution. In the case where it is present as a dry material, water is added in a given case by use of an aqueous acid.

The process of the invention is especially suitable for the stabilization of methionine which has been produced in the usual way by hydrolysis of the hydantoin (5($\beta$-methylmercaptoethyl)-hydantoin) in alkaline medium, e.g., aqueous potassium carbonate, potassium bicarbonate, sodium carbonate, sodium bicarbonate, sodium hydroxide and potassium hydroxide, and has been separated by neutralization of the reaction mixture with acid, e.g. carbon dioxide, acetic acid, formic acid, propionic acid, hydrochloric acid, sulfuric acid. Such a methionine generally contains impurities in an amount of up to 2%. The impurities are chiefly the byproducts occurring in the hydrolysis and the inorganic salts formed in the separation of the methionine from the solution. The process of the invention is especially suited for the stabilization of methionine produced for example by the process of German Pat. No. 1,906,405 or corresponding British Pat. No. 1,296,347 by hydrolysis of 5($\beta$-methylmercaptoethyl) hydantoin in an alkali carbonate, e.g., sodium carbonate or potassium carbonate, containing aqueous medium and recovered by neutralization of the reaction mixture by means of carbon dioxide. Thus it is suitable to stabilize methionine produced in each of examples 1, 2, 3, 4 and 5 of German Pat. No. 1,906,405 and British Pat. No. 1,296,347.

It is advantageous generally to stabilize the wet methionine as it is separated out of the reaction mixture resulting from the hydrolysis of the hydantoin. The methionine is freed as much as possible from adhering mother liquor suitably by filtration with suction and if necessary one or more washings with water, and then adjusted to the desired pH by spraying with the acid. It is advantageous to use dilute aqueous acids, for example sulfuric acid as a 1 to 20% solution and to thoroughly intimately mix the methionine with the acid during addition of the acid, for example, using a mixing drum.

The process of the invention can also be used to purify methionine prepared by the hydrolysis of alpha amino gamma methylmercaptobutyronitrile, for example as produced in example 1 of Kirkpatrick U.S. Pat. No. 2,443,391 or in Kralovec U.S. Pat. No. 2,504,425 examples 1, 2, 3, and 4. The entire disclosure of Kralovec is hereby incorporated by reference.

Unless otherwise indicated, all parts and percentages are by weight.

EXAMPLE 1

There was employed a commercially available methionine containing 99.1% methionine. The pH of the methionine, measured on a 2 gram sample in 50 ml of water was 5.8. 500 grams of the methionine in a mixture was sprayed with 125 ml of water and 2.5 ml of 5% sulfuric acid. The methionine was then dried at 70°C. It had a pH of 3.9 as measured on a 2 gram sample in 50 ml of water. After storage for 5 months at 30°C, it had an unchanged normal odor, light color and good pourability. A portion of the commercial material which was not treated with acid after the same period of storage had a strong odor and a changed color.

EXAMPLE 2

There was produced methionine by the hydrolysis with potassium carbonate of the corresponding hydantoin, specifically 5-(beta-methylmercaptoethyl)-hydantoin, precipitated by saturation of the reaction mixture with carbon dioxide, filtering and washing with water, e.g. note German Pat. No. 1,906,405 and British Pat. No. 1,296,347. The wet methionine recovered had 24% of adhering water and had a methionine content of 99.3% based on the dry material. The pH value measured on a 2 gram sample of the dry material in 50 ml of water was 7.8. 500 grams of the wet methionine were mixed with 29 ml of 5% sulfuric acid. The methionine was then dried at 70°C. A 2 gram sample in 50 ml of water had a pH of 4.7. After storing for 5 months at 30°C it had a normal odor, light color and a good pourability. A portion of the wet methionine was not treated with acid but dried directly at 70°C. After the same period of storing this portion had a strong odor, changed color and poor pourability.

Specifically, the process of the present invention can be carried out in the manner described in example 2 by mixing the wet methionine in each of the following examples A–E with sufficient sulfuric acid to impart a pH of 4.7 to a 2 gram sample of the methionine (after drying) in 50 ml of water.

EXAMPLE A 314 g. of an aqueous solution containing 86 g. of 5-($\beta$-methylmercaptoethyl)-hydantoin are added to a recycled mother liquor containing 327 g. of water, 60 g. of potassium carbonate, 27 g. of potassium hydrogen carbonate, 20 g. of methionine and 0.2 g. of 5-($\beta$-methylmercaptoethyl)-hydantoin.

The mixture is heated to 170°C in an autoclave equipped with stirring mechanism and held at this temperature for 40 minutes. The pressure is 7 atms. During this period a total of 212 g. of vapors consisting of steam, ammonia and carbon dioxide, is removed and collected. The reaction is over when no more ammonia passes over.

After venting and cooling at 100°C, the reaction solution has 0.2 g. of active carbon added to it and after further cooling to 15°C is filtered. Methionine is precipitated from the filtrate by introducing carbon dioxide in a first stage at normal pressure and in a second stage under an excess pressure of 3 atms. The solution absorbs 40 g. of carbon dioxide. The pH-value falls from 11.5 to 7.5. The methionine precipitated is filtered off and washed with 100 g. of water. 73 G. of methionine are obtained, corresponding to a yield of 99%, based on the hydantoin used. The methionine contains 0.5% of potassium hydrogen carbonate as impurity.

EXAMPLE B

285 Ml of an aqueous solution containing 81 g. of 5-($\beta$-methylmercaptoethyl)-hydrantoin are added to 1200 ml of an aqueous solution containing 110 g. of potassium carbonate and 50 g. of methionine in solution. The mixture is heated for 4 hours at 135° to 140°C under a pressure of from 2 to 3 atms., while 150 to 170 ml per hour of ammonia solution distill over together with carbon dioxide.

To precipitate methionine, the procedure described in Example A is adopted. The pH-value is lowered from 11.6 to 7.6 by introducing carbon dioxide into the solution.

69 G. of methionine obtained, corresponding to a yield of 99.5%, based on the hydantoin used. The methionine is 99.4% pure and has a melting point of from 272° to 273°C.

EXAMPLE C

The procedure is as in Example B except that the 1200 ml of starting solution contain 220 g. of potassium hydrogen carbonate and 55 g. of methionine. The reaction is carried out over a period of 3.5 hours at 140° to 145° C and at 4.5 to 5.5 atms. The yield and purity of the methionine obtained are the same as in Example B.

EXAMPLE D

1620 G. of 5-($\beta$-methylmercaptoethyl)-hydantoin in 5 liters of water are added to 30 litres of an aqueous solution containing 1600 g. of sodium methioninate and 2360 g. of sodium hydrogen carbonate. The solution is heated for 4 hours to 145°–150°C. The pressure is between 4.5 and 5 atms. at the beginning of the reaction and between 1 and 1.5 atms. at the end of the reaction. 3 to 3.2 liters per hour of aqueous ammonia solution are run off together with carbon dioxide.

After cooling to 15°C, the reaction solution is diluted with water to 25 liters. Methionine is precipitated by introducing carbon dioxide. The pH-value of the solution falls from 11.2 to 7.4 and, following the introduction of carbon dioxide at 3 atms. to 7.3.

EXAMPLE E

A solution of 100 g. of potassium hydrogen carbonate, 28 kg. of methionine and 41 kg. of 5-($\beta$-methylmercaptoethyl)-hydantoin in 400 liters of water is fed hourly by means of a metering pump into a continuous-cycle pressure apparatus consisting of three pressure-tight rotary evaporators arranged one behind the other.

The solution is continuously prepared from recycled mother liquor by adding a 30% solution of 5-($\beta$-methylmercaptoethyl)-hydantoin in water. An average residence time of 2 to 2.5 hours at 155° to 160°C and an average residence time of 15 to 20 minutes at 175° to 180°C is required to obtain a quantitative reaction.

To remove the ammonia and carbon dioxide formed, 70 to 100 kg/hour of steam at 160° or 180°C are passed through the reaction mixture. In other respects, the procedure is substantially the same as in Example A.

34.8 kg of methionine per hour are obtained, corresponding to a yield of 99.1%, based on the hydantoin used.

Substantially the same result is obtained by passing nitrogen instead of steam through in order to remove the ammonia and carbon dioxide.

What is claimed is:

1. A process for stabilizing methionine containing contaminants occurring in its production, said methionine being in the wet condition and having a pH of at least 5 comprising adjusting the pH of the methionine to 3.0 to 4.9 and drying the thus pH adjusted methionine to recover storage stable dry methionine which upon dissoltion in water gives a pH of 3.0 to 4.9.

2. A process according to claim 1 wherein the pH is adjusted by addition of an acid supplying material which is inert to methionine.

3. A process of preparing storage stable methionine according to claim 2 wherein the methionine is prepared by the alkaline hydrolysis of (1) alpha amino gamma methylmercapto butyronitrile or (2) 5-(beta-methylmercaptoethyl) hydantoin, and containing residual impurities from said hydrolysis.

4. A process according to claim 3 wherein the alkaline hydrolysis product is neutralized and then is acidified to a pH of 3 to 4.9 in the presence of water.

5. A process according to claim 4 wherein the compound hydrolyzed is 5-(beta-methylmercaptoethyl) hydantoin.

6. A process according to claim 5 wherein the hydrolysis had been carried out in an aqueous alkali carbonate medium.

7. A process according to claim 5 wherein the alkali carbonate is sodium carbonate or potassium carbonate and the neutralization of the reaction mixture is carried out with carbon dioxide.

8. A process according to claim 7 wherein the pH of the methionine is adjusted to 4.3–4.8.

9. A process according to claim 8 wherein the pH is adjusted to 4.3 to 4.8 with sulfuric acid or sodium bisulfate.

* * * * *